United States Patent [19]

Umezawa et al.

[11] Patent Number: 4,530,998
[45] Date of Patent: Jul. 23, 1985

[54] 2'-DEOXYOXANOSINE

[75] Inventors: Hamao Umezawa; Tomio Takeuchi; Masaaki Ishizuka, all of Tokyo; Tomohisa Takita, Asaka; Nobuyoshi Shimada, Tokyo; Kuniki Kato, Saitama, all of Japan

[73] Assignee: Zaidan Hojin Biseibutsu Kagaku KenkyuKai, Tokyo, Japan

[21] Appl. No.: 586,348

[22] Filed: Mar. 5, 1984

[30] Foreign Application Priority Data

Mar. 14, 1983 [JP] Japan .................... 58-40802

[51] Int. Cl.³ ........................... C07H 19/04
[52] U.S. Cl. ...................... 536/24; 424/180
[58] Field of Search ................... 536/23, 24

[56] References Cited

U.S. PATENT DOCUMENTS 3,309,359  3/1967  Duschinsky et al. ............... 536/23
3,562,250  2/1971  Langen et al. .................... 536/23
3,919,193  11/1975  Mian et al. ...................... 536/24

OTHER PUBLICATIONS

Shimada et al, "The Journal of Antibiotics", vol. XXXIV, No. 9, 1981, pp. 1216–1218.

Primary Examiner—Johnnie R. Brown
Attorney, Agent, or Firm—Henry C. Nields

[57] ABSTRACT

This invention relates to 2'-deoxy-oxanosine represented by the following formula:

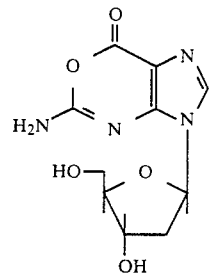

and process for the preparation thereof. This new compound exhibits a growth inhibiting action to gram-negative bacteria and has a carcinostatic action.

1 Claim, No Drawings

2'-DEOXYOXANOSINE

DETAILED DESCRIPTION OF THE INVENTION

This invention relates to 2'-deoxyoxanosine, a novel derivative of the antibiotic oxanosine having carcinostatic activity.

Oxanosine of the formula (I) was isolated by Hamao Umezawa et al. from the culture broth of Streptomyces capreolus MG265-CF3 (FERM-P No. 5735; A.T.C.C. 31963; see The Journal of Antibiotics, No. 34, p.1216–1218, 1981).

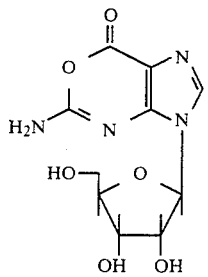

(I)

We, the inventors of this invention, used a naturally occurring substance, oxanosine of the formula (I), as the starting material to synthesize a 2'-deoxy-3', 5'-O-protected-oxanosine expressed by the general formula (II)

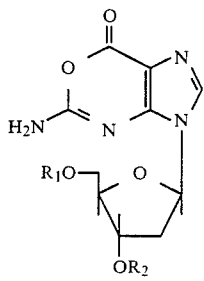

(II)

wherein $R_1$ and $R_2$ each represent a protective group for the hydroxyl group, followed by eliminating the protective groups at the 3'- and 5'-positions to synthesize 2'-deoxyoxanosine expressed by the formula (III).

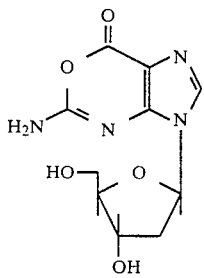

(III)

2'-Deoxyoxanosine of the formula (III) showed excellent antibacterial activity against gram-negative bacteria, and exhibited the action to inhibit the growth of leukemia L-1210 cells. These features anticipated its use as a novel pharmaceutical composition.

The physical and chemical properties of 2'-deoxyoxanosine were as follows:

(1) Melting point: 193°–196° C.
(2) IR spectrum $\nu_{max}^{Nujol}$: 3300, 3225, 3175, 3125, 1770, 1635, 1045, 1000, 945 cm$^{-1}$
(3) Mass spectrum (field desorption mass spectrometry) M/Z 268 (M+)
(4) NMR spectrum (CD$_3$OD): 6.22 ppm (1H,t,J=7 Hz) 7.98 ppm (1H,s)
(5) UV spectrum $\lambda_{max2}^{MeOH}$nm (log $\epsilon$): 286(3.91), 247(4.07)
(6) Specific rotation $[\alpha]_D^{20}$: −7.0° (c=0.4 MeOH)
(7) Elemental analysis, molecular formula and molecular weight:

Calcd.: C:44.91, H:4.47, N:20.75, Found: C:44.78, H:4.51, N:20.89, Molecular formula: C$_{10}$H$_{12}$N$_4$O$_5$ Molecular weight: 268. 2'-Deoxyoxanosine in accordance with the present invention had the following antibacterial spectrum on 0.5% peptone agar.

TABLE 1

| Antibacterial spectrum of 2'-deoxyoxanosine | |
|---|---|
| Strain | MIC (mcg/ml) |
| Staphylococcus aureus FDA209P | >100 |
| Staphylococcus aureus Simth | >100 |
| Micrococcus flavus FDA16 | >100 |
| Sarcina luteus PCI1001 | >100 |
| Bacillus subtilis PCI219 | >100 |
| Bacillus subtilis NRRLB-558 | >100 |
| Corynebacterium bovis 1810 | >100 |
| Escherichia coli NIHJ | 12.5 |
| Escherichia coli K-12 | 0.78 |
| Escherichia coli ML1628 (multiple resistant strain) | 3.12 |
| Shigella dysenteriae JS11910 | 1.56 |
| Shigella flexneri 4bJS11811 | 1.56 |
| Shigella sonnei JS11746 | 0.78 |
| Salmonella typhi T-63 | >100 |
| Salmonella enteritidis 1891 | >100 |
| Proteus vulgaris OX19 | <0.2 |
| Proteus mirabilis IFM OM-9 | 6.25 |
| Proteus rettgeri GN311 | 12.5 |
| Proteus rettgeri GN466 | 25 |
| Serratia marcescens | >100 |
| Pseudomonas aeruginosa A3 | >100 |
| Klebsiella pneumoniae PCI602 | >100 |
| Candida albicans 3147 | >100 |
| Mycobacterium 607 | >100 |

As shown in Table 1, 2'-deoxyoxanosine had a relatively high growth-inhibitory activity against such gram-negative bacteria as Escherichia coli NIHJ, E. coli K-12, E. coli ML1629 (a strain resistant to multiple drugs), Shigella dysenteriae JS11910, S. flexneri 4bJS11811, S. sonnei JS11746, Proteus vulgaris OX19, P. mirabilis IFM OM-9, P. rettgeri GN311 and P. rettgeri GN466, but did not show this activity against gram-positive bacteria.

A study of the cytotoxicity of 2'-deoxyoxanosine showed that its IC$_{50}$, the concentration inhibiting growth in 50% of leukemia L-1210 cells, was 0.15 μg/ml.

The acute toxicity (LD$_{50}$) of 2'-deoxyoxanosine in mice was 200 mg/kg (i.v.), a value representing lower toxicity than that of various known antibiotics similar in structure to nucleic acids.

The above findings make it clear that 2'-deoxyoxanosine is promising as a novel chemotherapeutic agent against Escherichia coli, species of Shigella and species of Proteus and as a novel carcinostatic agent.

2'-Deoxyoxanosine of the formula (III) of the present invention is synthesized according to the following reaction scheme:

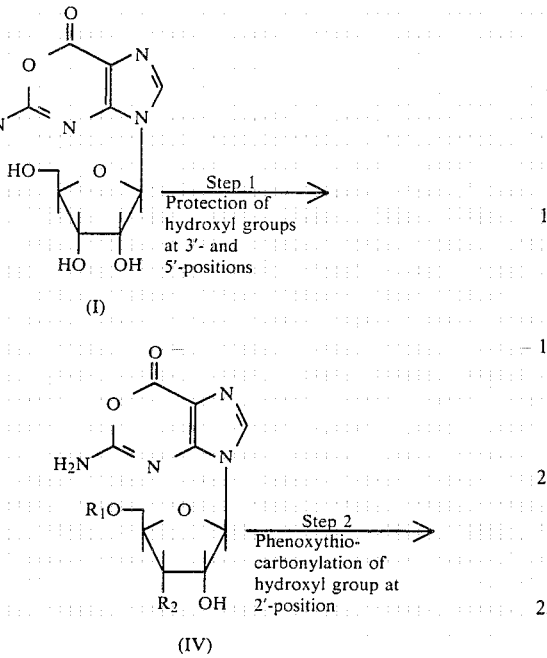

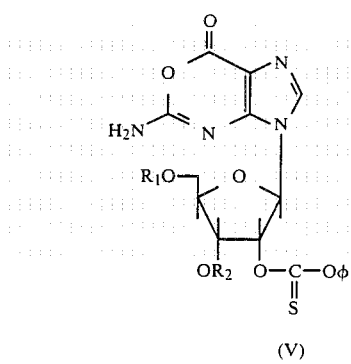

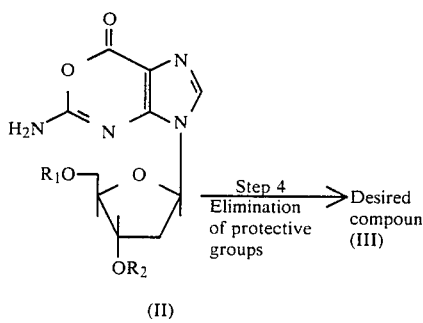

$R_1$, $R_2$: Protective group for a hydroxyl group.

In Step 1, the hydroxyl groups at the 3'- and 5'-positions of oxanosine are protected to form a 3',5'-O-diprotectedoxanosine expressed by the general formula (IV). The subsequent Step 2 is designed to phenoxythiocarbonylate the hydroxyl group at the 2'-position, thereby forming an oxanosine derivative expressed by the general formula (V).

This derivative is then reduced in Step 3 to eliminate the phenoxythiocarbonyloxy group at the 2'-positon, therby obtaining a 2'-deoxy-3',5'-O-diprotected oxanosine expressed by the general formula (II). Finally, the protective groups are eliminated in Step 4 to give the desired 2'-deoxyoxanosine of the formula (III).

Each step will be described in detail below.

STEP 1

The hydroxyl group at the 3'- and 5'-positions of the starting compound, oxanosine, can be protected in a customary manner. Various protective groups in wide use as protective groups for hydroxyl groups can be used for this purpose. Preferably, they should be those that can be eliminated under acidic or neutral conditions, because the desired compound to be obtained by the elimination of the protective groups in Step 4 is relatively unstable under basic conditions.

Examples of the protective groups are silyl groups such as a tert-butyldimethylsilyl group, a triisopropylsilyl group or a 1,1,3,3-tetraisopropyl-1,3-disilyl group.

Those protective groups can be introduced into oxanosine at the 3'- and 5'-positions by, say, reacting a silyl chloride (corresponding to the protective group) with oxanosine at a temperature of about $-10° \sim 50°$ C., preferably, $10° \sim 30°$ C. in a solvent in the presence of a basic catalyst such as pyridine, triethylamine or imidazole.

The solvent may be an aprotic solvent such a dioxane or dimethylformamide.

STEP 2

This step is intended to phenoxythiocarbonylate the hydroxyl group at the 2'-position. This reaction is performed in a solvent at room temperature or with cooling with the use of phenoxythiocarbonyl chloride as a phenoxythiocarbonylating agent in the presence of a basic catalyst such as triethylamine or 4-dimethylaminopyridine, preferably, 4-dimethylaminopyridine. The solvent may, for example, be an aprotic solvent such as acetonitrile, dichloromethane, dioxane or tetrahydrofran.

STEP 3

This step consists of a reaction for substitution the phenoxythiocarbonate group at the 2'-position by a hydrogen atom. This reaction is carried out by reducing the compound of the general formula (V) with a reducing agent, particularly, a tri-substituted-tin hydride.

Examples of the tri-substituted-tin hydride are trialkyltin hydrides such as triethyltin hydride or tri-n-butyltin hydride, and triphenyltin hydride. Preferred examples of the solvent to be used in the reaction are aprotic solvents, such as toluene, benzene, dioxane or tetrahydrofuran, which do not contain halogen atoms and which are difficult to reduce. The reaction is performed at 10°–150° C., preferably, 30°–100 C. To promote the reaction, it is preferred to add a free-radical initiator, such as $\alpha,\alpha'$-azobisisobutyronitrile (AIBN), to the reaction system.

STEP 4

2'-Deoxy-3',5'-O-diprotected-oxanosine of the general formula (II), obtained by the above step, is then deprived of the hydroxyl-protecting groups at the 3'- and 5'-positions. This elimination of the hydroxyl-protecting groups is performed by treating the compound under ordinary silyl-removing conditions, i.e., by treatment with a mineral acid such as hydrochloric acid or sulfuric acid or a fluorine compound such as potassium fluoride, tetrabutylammonium fluoride or hydrogen fluoride. This reaction is carried out at 0°–80° C., preferably 10–40C.°, in a solvent. The solvent is that stable to the fluorine compound, such as tetrahydrofuran, dioxane or methanol.

The above-described methods synthesize 2′-deoxyoxanosine, the intended compound of this invention. These methods and the properties of the resulting product will be described in more detail with reference to the following Example, in which NMR means nuclear magnetic resonance spectrum; IR, infrared absorption spectrum; UV, ultraviolet absorption spectrum; and MS, mass spectrum.

EXAMPLE (1) Synthesis of 3′,5′-O-(tetraisopropyldisiloxan-1,3-diyl) oxanosine 568 mg of oxanosine was dissolved in 10 ml of anhydrous pyridine, and 694 mg of or 1.1 equivalents of 1,3-dichloro-1,1,3,3-tetraisopropyldisiloxane was added to the solution. The mixture was reacted for 4 hours at room temperature with stirring. After the reaction ended, the solvent was evaporated under reduced pressure, and 100 ml of ethyl acetate was added to the residue. The ethyl acetate solution was washed sequentially with 0.1N hydrochloric acid, water, and a saturated solution of sodium chloride, and dried over anhydrous sodium sulfate. The solvent was evaporated from the residue under reduced pressure to obtain viscous matter. This matter was chromatographed on a silica gel column, and eluted with chloroform-methanol (20:1). 800 mg of a crystalline substance was isolated from the eluate. Yield: 76%.

mp: 199°–202° C.
IR $\nu_{max}^{Nujol}$: 3400, 3340, 3180, 3140, 1755, 1670, 1165, 1050, 890 cm$^{-1}$
MS (SIMS): M/Z 527 (M+H)$^+$
NMR (CDCl$_3$): 5.78 ppm (1H,S), 7.72 ppm (1H,S)
UV $\lambda_{max}^{MeOH}$ mn (log ε): 286 (3.93), 247 (4.11)

(2) Synthesis of 2′-O-phenoxythiocarbonyl-3′,5′-O-(tetraisopropldisiloxan-1,3-diyl)oxanosine 400 mg of 3′,5′-O-(tetraisopropyldisiloxan-1,3-diyl)oxanosine and 279 mg or 3 equivalents or 4-dimethylaminopyridine were dissolved in 5 ml of anhydrous acetonitrile. 393 mg or 3 equivalents of phenyl chlorothionocarbonate was aded at a time to the solution. The mixture was stirred for 1 hour at room temperature. After the reaction was completed, the solvent was evaporated under reduced pressure. 80 ml of ethyl acetate was added to the residue. The ethyl acetate solution was washed sequentially with 0.1N hydrochloric acid, water, and a saturated solution of sodium chloride, and dried over anhydrous sodium sulfate. The residue was evaporated under reduced pressure to remove the solvent. The resulting matter was chromatographed on a silica gel column, and eluted with chloroform-methanol (20:1). The treatment of the eluate gave 265 mg of the desired product as crystals (yield: 53%) and 141 mg of the starting material (recovery: 27%).

mp: 185°–187° C.
IR $\nu_{max}^{Nujol}$: 3325, 3200, 1770, 1760, 1690, 1060, 1042, 890, 770 cm$^{-1}$
MS (SIMS): M/Z 663 (M+H)$^+$
NMR (CDCl$_3$): 6.20 ppm (1H,d,J=5 Hz), 7.71 ppm (1H,S)
UV $\lambda_{max}^{MeOH}$ mn (log ε): 285 (4.02), 242 (4.22)

(3) Synthesis of 2′-deoxy3′,5′-O-(tetraisopropyldisiloxan-1,3-diyl)oxanosine 200 mg of 2′-O-phenoxythiocarbonyl-3′,5′-O-(tetraisopropyldisiloxan-1,3-diyl)oxanosine, 175 mg or 2 equivalents of tributyltin hydride, and 20 mg of α,α′-azobisisobutyronitrile were dissolved in 5 mg of dry toluene. The solution was reacted, with stirring, for 2 hours at 75° C. in a stream of nitrogen. After the reaction was completed, the solvent was evaporated under reduced pressure. The residue was chromatographed on a silica gel column, and eluted with chloroform-methanol (20:1). The treatment of the eluate gave 126 mg of a crystalline substance. Yield: 82%.

mp: 205°–207° C.
IR $\nu_{max}^{Nujol}$: 3325, 3175, 1760, 1685, 1150, 1120, 1050, 1035, 890 cm$^{-1}$
MS (SIMS): M/Z 511 (M+H)$^+$
NMR (CDCl$_3$): 6.05 ppm (1H,t,J=6 Hz), 7.73 ppm (1H,S)
$\lambda_{max}^{MeOH}$ mn (log ε): 286 (3.96), 247 (4.13)

(4) Synthesis of 2′-deoxyoxanosine 100 mg of 2′-deoxy-3′,5′-O-(tetraisopropyldisiloxan-1,3-diyl)oxanosine was dissolved in 2 ml of tetrahydrofuran. 400 μl of a 1 mol solution of teterabutylammonium fluoride (103 mg or 2 equivalents) in tetrahydrofuran was added to the solution, and the mixture was reacted for 10 minutes at room temperature with stirring. After the reaction was completed, the solvent was evaporated under reduced pressure. The residue was chromatographed on a silica gel column, and eluted with chloroform-methanol (4:1). Treatment of the eluate gave 43 mg of the desired product as crystals. Yield: 82%.

What is claimed is:

1. 2′-Deoxyoxanosine expressed by the following formula:

* * * * *